US012629326B2

(12) United States Patent
Yagoda

(10) Patent No.: US 12,629,326 B2
(45) Date of Patent: May 19, 2026

(54) SILICONE SUBSTITUTE NATURAL ADDITIVE COMPOSITION, PROCESS FOR OBTAINING THE SAME AND ITS USE

(71) Applicant: MAIAN INDUSTRIA DE PRODUTOS QUIMICOS LTDA., Jardim Alvorada (BR)

(72) Inventor: Angel Dachs Yagoda, São Paulo (BR)

(73) Assignee: MAIAN INDUSTRIA DE PRODUTOS QUIMICOS LTDA., São Paulo (BR)

( * ) Notice: Subject to any disclaimer, the term of this patent is extended or adjusted under 35 U.S.C. 154(b) by 656 days.

(21) Appl. No.: 17/635,842

(22) PCT Filed: Sep. 11, 2019

(86) PCT No.: PCT/BR2019/050388

§ 371 (c)(1),
(2) Date: Feb. 16, 2022

(87) PCT Pub. No.: WO2021/046622

PCT Pub. Date: Mar. 18, 2021

(65) Prior Publication Data

US 2022/0296487 A1      Sep. 22, 2022

(51) Int. Cl.
| | |
|---|---|
| *A61K 8/60* | (2006.01) |
| *A61G 5/00* | (2006.01) |
| *A61K 8/34* | (2006.01) |
| *A61Q 19/00* | (2006.01) |

(52) U.S. Cl.
CPC ................. *A61K 8/60* (2013.01); *A61G 5/00* (2013.01); *A61K 8/34* (2013.01); *A61Q 19/00* (2013.01)

(58) Field of Classification Search
CPC ........ A61K 8/60; A61K 8/34; A61K 2800/10; A61K 2800/34; A61K 8/345; A61K 8/25; A61K 8/37; A61K 8/73; A61Q 5/00; A61Q 19/00; A61Q 5/12; A61Q 1/00; A61Q 17/00; C09G 1/04
See application file for complete search history.

(56) References Cited

U.S. PATENT DOCUMENTS

| | | | | | |
|---|---|---|---|---|---|
| 9,757,322 | B2 * | 9/2017 | Yoshida | ................... | A61K 8/39 |
| 2002/0111281 | A1 * | 8/2002 | Vishnupad | ............. | A61Q 19/00 |
| | | | | | 510/130 |
| 2005/0186281 | A1 * | 8/2005 | Lalum | .................. | A61Q 17/005 |
| | | | | | 424/487 |
| 2007/0104665 | A1 * | 5/2007 | Jones | ........................ | A61K 8/06 |
| | | | | | 424/62 |
| 2009/0074697 | A1 | 3/2009 | Huynh | | |
| 2011/0150812 | A1 | 6/2011 | Mecca | | |
| 2012/0064136 | A1 * | 3/2012 | Baker, Jr. | ............... | A61K 8/922 |
| | | | | | 514/159 |
| 2012/0308672 | A1 * | 12/2012 | Van | ........................ | A61P 17/00 |
| | | | | | 424/725 |

FOREIGN PATENT DOCUMENTS

| | | | |
|---|---|---|---|
| CN | 105342874 | 2/2016 | |
| FR | 2961690 A1 * | 12/2011 | ............. A61K 8/345 |

OTHER PUBLICATIONS

Slavin. Carbohydrates. Adv. Nutr. 5: 760-761, 2014. (Year: 2014).*
USDA Glycerides (mono and di). 2015 (Year: 2015).*
EFSA. Re-evaluation of silicon dioxide (E 551) as a food additive. EFSA Journal 2018;16(1):5088 (Year: 2018).*
Fiume et. al. "Safety Assessment of Monosaccharides, Disaccharides, and Related Ingredients as Used in Cosmetics" International Journal of Toxicology 2019, vol. 38(Supplement 1) 5S-38S. (Year: 2019).*
Grenby et. al. "Properties of maltodextrins and glucose syrups in experiments in vitro and in the diets of laboratory animals, relating to dental health" British Journal of Nutrition (2000), 84, 565-574. (Year: 2000).*
FR2961690A1—machine translation; Isoir et. al. "Use of a mannose monosaccharide as skin conditioning agent and in cosmetic and/or dermatological composition for treating skin, preferably dry skin" 2011. (Year: 2011).*
Fiume (International Journal of Toxicology, 2019)—from previous office action (Year: 2019).*
FR2961690A1—machine translation—from previous office action (Year: 2011).*
Grenby (British Journal of Nutrition, 2000)—from previous office action (Year: 2000).*
CIR "Safety Assessment of Polysaccharide Gums as Used in Cosmetics" 2015 (Year: 2015).*
FR2961690A1—machine translation. "Use of a mannose monosaccharide as skin conditioning agent and in cosmetic and/or dermatological composition for treating skin, preferably dry skin." 2011. (Year: 2011).*
Fiume. "Safety Assessment of Monosaccharides, Disaccharides, and Related Ingredients as Used in Cosmetics" International Journal of Toxicology 2019, vol. 38(Supplement 1) 5S-38S. (Year: 2019).*
Grenby "Properties of maltodextrins and glucose syrups in experiments in vitro and in the diets of laboratory animals, relating to dental health" British Journal of Nutrition (2000), 84, 565-574. (Year: 2000).*

(Continued)

*Primary Examiner* — Sean M Basquill
*Assistant Examiner* — Rajan Pragani
(74) *Attorney, Agent, or Firm* — FisherBroyles, LLP; Susan M. Oiler

(57) ABSTRACT

A natural additive composition capable of replacing silicone components in a wide variety of types of application, preferably in the field of cosmetic, veterinary cosmetic, dermocosmetic products has, in terms of percent by weight of the total weight of the composition: (a) 0.5% to 80% polysaccharides, monosaccharides and derivatives thereof; (b) 10% to 99.5% monohydric alcohols, polyhydric alcohols, unsaturated aliphatic alcohols, glycerides; and (c) 0% to 40% components depending on the type of application, which can be abrasives, emollients, rheology modifiers, moisture absorbers, etc.

8 Claims, 8 Drawing Sheets

(56) References Cited

OTHER PUBLICATIONS

PCT/BR2019/050388, International Search Report, Jun. 6, 2020, (p. 3).

PCT/BR2019/050388, International Written Opinion, on or after Jul. 10, 2021, (p. 6).

Pneu Pretinho—Como Fazer, Apr. 16, 2016, https://www.youtube.com/watch?v=o4rorNH-nis.

Vincience biofunctionals 2017 synopsis for skin care and hair care application—cotton bloom 5S, 2017, https://www.ashland.com/file_source/Ashland/Industries/Personal%20and%20Home%20Care/Articles/PC-12152.11_Vincience.pdf.

Como fazer pretinho para carro, Dec. 5, 2017. http://drlavatudo.com/blog/pretinho-para-carro/ (Webpage no longer available).

Como fazer pretinho caseiro, Mar. 1, 2018, https://www.youtube.com/watch?v=wLqbCLVd50I.

Hestrin et al., Differentiation betweenGlucose, Galactose and Mannose by a Colour Reaction, Nature Portfolio, 1946, 3 pages, vol. 158 Issue 4003.

Dumouilla et al., Online analysis of D-glucose and D-mannose aqueous mixtures using Raman spectroscopy: an in silico and experimental approach, Bioengineered, Jun. 22, 2021, pp. 4420-4431, vol. 12 Issue 1.

Rhys et al., Glucose and Mannose: a Link between Hydration and Sweetness, 18 pages, reference date: 2017—https://pubs.acs.org/doi/full/10.1021/acs. jpcb. 7b03919.

* cited by examiner

APPLYING AND RINSING                                    Example 1
CYCLOPENTASILOXANE AND DIMETHICONE

DRY HAIR                                    Example 1
CYCLOPENTASILOXANE AND DIMETHICONE

APPLAYING AND RINSING
Example 2  DIMETHICONE 350

SILIKE 350 GPG          DIMETHICONE 350

DRY HAIR
Example 2          DIMETHICONE 350

SILIKE 350 GPG          DIMETHICONE 350

Test on the Skin
Example 4 x Dimethicone 200

APPLYING AND RINSING
Example 5 Dimethicone 5000

DRY HAIR
Example 5  Dimethicone 5000

APPLYING AND RINSING
Example 6  Cyclopentasiloxane and Dimethicone

DRY HAIR
Example 6  Cyclopentasiloxane and Dimethicone

APPLYING AND RINSING

Example 7 x Amodimethicone (and) Trideceth-12 (and)
Cetrimonium Chloride

DRY HAIR

Example 7 x Amodimethicone (and) Trideceth-12 (and)
Cetrimonium Chloride

SILICONE SUBSTITUTE NATURAL ADDITIVE COMPOSITION, PROCESS FOR OBTAINING THE SAME AND ITS USE

CROSS-REFERENCE TO RELATED APPLICATIONS

The present invention is filed under 35 U.S.C. § 371 as the U.S. national phase of International Patent Application No. PCT/BR2019/050388, filed Sep. 11, 2019, which designated the United States, which is hereby incorporated in its entirety including all tables, figures, and claims.

APPLICATION FIELD

The present invention relates to a natural additive composition capable of replacing silicone in the most various types of applications, preferably in the field of cosmetic products, veterinary cosmetics, dermocosmetics, etc.

PRIOR ART

The cosmetic industry has grown a lot in the past few decades thanks to the use of a synthetic component employed in the vast majority of formulations called generally silicone.

Among the class of silicones, polydimethylsiloxane (PDMS), also referred to as dimethylpolysiloxane or dimethicone or dimethicone, is a very useful organosilicon polymer thanks to its unusual rheological properties, of light, inert, non-toxic and non-flammable properties, which has been in the form of silicone oil.

Their applications are diverse, in contact lenses, medical devices, elastomers, cosmetics in general as shampoos (because it makes the hair brighter and slippery), moisturizing creams, foods (as antifoam agent), for caulking, lubricants or even on heat resistant tiles or mould.

The PDMS is manufactured in many degrees of polymerization and can be in the form of a thin pourable liquid to a thick, rubberized semi-solid.

The PDMS is flexible and viscoelastic, in cosmetic applications delivering good sensory properties to the skin and hair.

Another component of the class of silicones are cyclomethicones, which, in contrast to dimethicone that are linear and non-evaporating siloxanes, are cyclic and when employed in the form of methyl siloxanes are in liquid form with low viscosity and high volatility, and in addition to being emollients for the skin, may even be employed in cleaning solvents.

The polysiloxanes are polymers that include any synthetic compound constituted by repeating units of siloxane, which is a chain of alternated silicon atoms and oxygen atoms, combined with carbon, hydrogen, and sometimes other elements. They are typically heat resistant and liquid or rubbery, and are used in sealants, adhesives, lubricants, medicines, kitchen utensils and thermal and electrical insulation. Some common forms include silicone oil, silicone grease, silicone rubber, silicone resin and silicone gum mass.

The overall demand for silicones approached $12.5 billion in 2008, approximately 4% above the previous year. It has continued for a similar growth in the next years, achieving $13.5 billion in 2010. The annual growth should be driven by broader applications, introduction of new products and greater awareness of the use of more ecological materials.

The major world manufacturers of silicone materials belong to three regional organizations: the European Silicone Center (CES) in Brussels, Belgium; the Environmental Health and Safety Council (SEHSC) in Herndon, Virginia, USA; and The Association of the Japan Silicone Industry (SIAJ) in Tokyo, Japan. Dow Corning Silicones, Evonik Industries, Momentive Performance Materials, Milliken and Company (SiVance Specialty Silicones), Shin-Etsu Silicones, Wacker Chemie, Bluer Silicones, JNC Corporation, Wacker Asahikasei Silicone and Dow Corning Toray represent the collective members of these organizations. A fourth organization, the Global Silicone Council (GSC) acts as an umbrella structure over regional organization. All four are non-profit ones, having no commercial role; their major missions are to promote the silicones safety from a health, safety, and environment perspective. Because the European chemical industry is preparing to implement the Registration, Evaluation, Authorization and Restriction of Chemicals (REACH) substances legislation, the CES will limit the formation of a consortium of producers and importers of silicones, silanes and siloxanes to facilitate sharing data and costs.

Other studies point that silicone compounds are diffused into the environment. Specific silicone compounds, cyclic siloxanes D4 and D5, are air and water pollutants and have negative effects on the health of the animals tested. They are used in various personal care products. The European Agency of Chemicals concluded that "D4 is a persistent, bioaccumulative and toxic (PBT) substance and D5 is A very persistent and very bioaccumulative substance (vPvB). Other silicones readily biodegrade, in a process that is accelerated by a plurality of catalysts, including clays. Cyclic silicones have been shown to involve the occurrence of silanols during biodegradation in mammals. The resulting silanediols and silanetriols are capable of inhibiting hydrolytic enzymes such as thermolysine, and acetylcholinesterase, however, the doses required for inhibition are in orders of magnitude higher than the cumulative exposure to consumption products containing cyclomethicones.

It has been studied that around 200° C. in an oxygen-containing atmosphere, PDMS (Polydimethylsiloxane) releases formaldehyde traces (less than other common materials, such as polyethylene). At 200° C., it has been verified that silicones have less formaldehyde generation than mineral oil and plastic (less than 3 to 48 µg $CH_2O/(g \cdot h)$ for high consistency silicone rubber, versus about 400 µg $CH_2O/(g \cdot h)$ for plastics and mineral oil). Around 250° C., large amounts of formaldehyde were produced for all silicones (1200 to 4,600 µg $CH_2O/(g \cdot h)$). These formaldehyde emissions are considered problematic for our environment.

But urge that a substituent is developed for the silicone, a synthetic compound, of low biodegradability in the environment, and which generates no-sustainable effluents to the planet.

These considerations are some of the studies that have been questioned nowadays worldwide and they were the reason that has led the Applicant to make this important development. The product according to the present invention is natural and our planet produces its raw material in large scale. It employs monosaccharides, or polysaccharides, or derivatives thereof as the main raw material.

The person skilled in the art has already accomplished efforts to find a substitute for silicone. The published document US 2005/0260150 describes low viscosity esters that can be used as low viscosity silicone fluid substitutes. The published document US 2004/0241200 describes mixtures of certain synthetic esters with volatile hydrocarbons that are useful for the substitution of volatile tetramers and cyclomethicones pentamers. The published document US 2009/0123398 describes mixtures of hydrocarbon fluids useful for the substitution of volatile tetramers and cyclomethicones pentamers.

The document EP3360600 relates to a silicone natural substitute for silicone fluids in personal formulations comprising a mixture of at least one polymeric ester and at least one non-polymeric ester. The polymeric ester is a product of the esterification reaction of (i) at least one first dicarboxylic acid, (ii) at least one first mono-functional alcohol or mono-functional carboxylic acid, and (iii) glycerin or derivatives thereof. The non-polymeric ester is a product of the esterification reaction of at (i) with at least one second dicarboxylic acid and (ii) at least one second mono-functional alcohol.

But none of the inventions solved a major problem: a composition capable of substituting silicone in its most diverse applications. It is estimated that this new industry keeps in strong growth and, therefore, the Applicant has developed a natural and biodegradable product, which by being a product of plant origin that does not cause problems for the health of humans or animals, or to the environment, can be considered a large relevance innovation.

OBJECTS OF THE INVENTION

Applicant developed a natural product formulation to substitute what is known in the market as silicone. The objective was to solve a growing world problem, over which today's entrepreneurs cannot stand back. The environmental impact is being a large threat and the search for options as per the entrepreneur's part must be immediate. We are devastating forests, contaminating rivers, contaminating the air, and we ourselves are the must harmed ones. Luckily, there is a concern for the consumer, which is driving the businesses to innovate and find solutions.

Within the scope of silicones that we use, inhale, ingest, daily, without our knowledge, there are some concerns, and some silicons have already been prohibited in Europe and Canada.

Applicant has developed a natural composition capable of replacing silicone in several types of industrial applications, presenting the following advantages:
  good rheological properties;
  colorless and odorless product;
  non-flammable;
  natural product, which does not generate non-biodegradable effluents;
  sustainable;
  it has good sensory cosmetic properties and after applied to the skin, and to hair as: conditioning, softness, ease of combing, detangling, hydration, hair feel and spreadability;
  low cost of raw materials;
  low cost of the final product.

BRIEF DESCRIPTION OF THE INVENTION

The silicone substitute natural composition according to the invention comprises in mass relative to the total mass of the composition:
  (a) from 0.5 to 80% of polysaccharides, monosaccharides, and derivatives thereof;
  (b) from 10% to 99.5% monohydric alcohols, polyhydric alcohols, unsaturated aliphatic alcohols, glycerides;

(c) from 0 to 40% of components according to the type of application, which may be abrasives, emollients, rheology modifiers, moisture absorbers, etc. and method for obtaining such a composition.

DESCRIPTION OF THE FIGURES

Attached herewith are found the figures that illustrate the results achieved with experiments of the invention.

DETAILED DESCRIPTION OF THE INVENTION

Figures 1, 2:
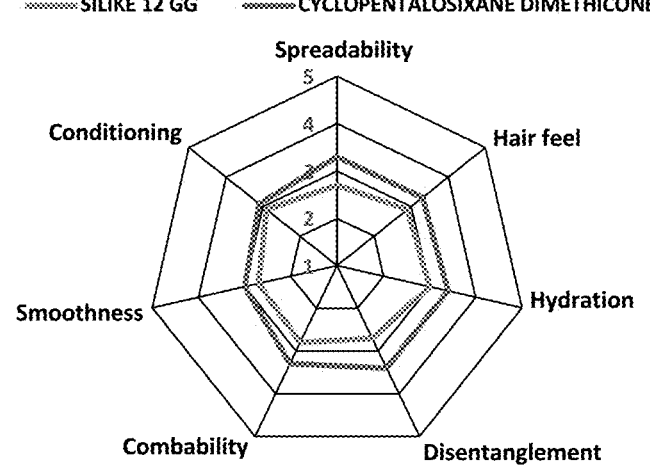
FIG. 1 is a comparative graph of properties after applying and rinsing hair with the composition according to the invention and cyclopentasiloxane and dimethicone.
FIG. 2 is a comparative graph of properties after applying and rinsing dry hair with the composition according to the invention and cyclopentasiloxane and dimethicone.

The present invention employs in its composition 0.5 to 80% by weight in mass relative to the total mass of the composition of polysaccharide, monosaccharides, and derivatives thereof, selected from the group comprising: sucrose, lactose, fructose, glucose, galactose, maltose, arabinose, xylose, mannose, sucrose, sorbitol, glucose, among others. Preferably, glucose is employed.

Corn glucose, also referred to as glucose syrup, is a food syrup obtained by hydrolysis of the corn starch. It is mainly a concentrated source of calories with very little nutritional value. In recent years, corn glucose has emerged as a popular substitute for sugar. The demand for corn glucose in the food processing industry has also witnessed a strong growth in recent years. It is used primarily as a key ingredient in foods commercially prepared to improve taste, improving color, adding volume, and providing a smooth texture to food. As aid in preventing sugar crystallization, corn glucose is widely used in confections, jams, canned fruits, ice creams, ice creams, beverages, dairy desserts, cookies, candies, cereals, ketchup, sauces, vitaminic tonic and cough medicaments. According to the IMARC Group, the overall corn glucose market has reached a volume of about 3.6 million tons in 2018, representing a CAGR of almost 1% for 2011-2018.

Corn glucose may be employable as carbohydrate according to the invention.

Glucose is a simple sugar of molecular formula $C_6H_{12}O_6$. Glucose is the most abundant monosaccharide, being produced naturally mainly by plants and algae during photosynthesis of water and carbon dioxide, using solar energy.

The glucose employed in the composition according to the invention can be employed in the form of dry glucose syrup, which is obtained by spray drying of syrups from carbon hydrates concentrates derived from the partial hydrolysis of the starch.

The composition also employs 10% to 99.5% of monohydric alcohols, polyhydric alcohols, unsaturated aliphatic alcohols, glycerides, selected from the group comprising: ethylene glycol, propylene glycol, glycerin, butylene glycol, ethyl hexyl glycerin, caprylyl glycol, etc. Preferably, propylene glycol and/or glycerin is used.

The composition may also present another component (c) selected from the group comprising fatty acid derivatives selected from the group comprising the acid: lauryl, cetyl, stearyl, myristyl, oleyl, stearic, lauric, myristic, palmitic, oleic; linoleic. Preferably, isopropyl palmitate and/or isoamyl laurate are used.

Component (c) can also be an abrasive, such as silica.

One embodiment of the silicone substitute natural composition according to the invention comprises in mass relative to the total mass of the composition:

(a) from 0.5% to 70% of monosaccharides, polysaccharides and derivatives thereof are selected from the group comprising: sucrose, lactose, fructose, glucose, galactose, maltose, arabinose, xylose, mannose, sucrose, sorbitol and glucose;

(b) from 10% to 99.5% of ethylene glycol, propylene glycol, glycerin, butylene glycol;

(c) from 0 to 40% of other components according to the type of application, which may be abrasives, emollients, rheology modifiers, moisture absorbers, etc.

Another embodiment of the silicone substitute natural composition according to the invention comprises in mass relative to the total mass of the composition:

(a) from 0.5% to 70% of glucose;

(b) from 10% to 99.5% of propylene glycol and/or glycerin;

(c) from 0 to 40% of fatty acid esters and/or silica.

A preferred embodiment of the silicone substitute natural composition according to the invention comprises in mass relative to the total mass of the composition:

(a) from 2% to 60% of glucose;

(b) from 20 to 99.5% of propylene glycol and/or glycerin;

(c) from 0 to 35% of fatty acid esters, silica.

The process for obtaining the silicone substitute natural composition according to the invention comprises the following steps:

(a) in a reactor, add from 10% to 99.5% by mass of monohydric alcohols, polyhydric alcohols, unsaturated aliphatic alcohols, glycerides, and raise the temperature from 60° C. to 80° C.;

(b) stir for 30 to 50 minutes and soon after slowly add from 0.5% to 70% by mass of monosaccharides, polysaccharides and derivatives thereof until a homogeneous mixture is achieved between 30 to 50 minutes;

(c) add from 0% to 40% by mass of other components according to the type of application, such as abrasives, emollients, fatty acid esters, rheology modifiers, moisture absorbents, etc., and mix from 30 to 50 minutes.

Another process for obtaining the silicone substitute natural composition according to the invention comprises the following steps:

(a) in a reactor, add from 10% to 99.5% by mass of emollients and/or solvents selected from the group comprising: ethylene glycol, propylene glycol, glycerin, butylene glycol and raise the temperature from 60° C. to 80° C.;

(b) stir for 30 to 50 minutes and soon after slowly add from 0.5% to 60% by mass of monosaccharides, polysaccharides and derivatives thereof selected from the group comprising: sucrose, lactose, fructose, glucose, galactose, maltose, arabinose, xylose, mannose, sucrose, sorbitol and glucose; until a homogeneous mixture is achieved between 30 to 50 minutes;

(c) add from 0% to 40% by mass of other components according to the type of application, such as abrasives, emollients, fatty acid esters, rheology modifiers, moisture absorbents, etc., and mix from 30 to 50 minutes.

Another preferred embodiment of the process for obtaining the silicone substitute natural composition according to the invention comprises the following steps:

(a) in a reactor, add from 10% to 99.5% by mass of propylene glycol and/or glycerin and raise the temperature from 60° C. to 80° C.;

(b) stir for 30 to 50 minutes and soon after slowly add from 0.5 to 60% by mass of glucose until a homogeneous mixture is achieved between 30 to 50 minutes;

(c) add from 0 to 40% by weight of fatty acid esters and/or drying agent.

Glucose is slowly added, since it has to be added very slowly to achieve good dispersion. The reactor rotation can be between 150 and 320 rpm, preferably between 200 and 300 rpm.

The use of the silicone substitute natural composition according to the invention in cosmetic products, veterinary cosmetics, dermocosmetics, automotive, and the like, substantially free of silicone. By "substantially free of silicone" is meant that the formulations are formulated without the inclusion of initial compounds containing silicone groups.

The following is a few examples of embodiments of the invention that are not to be taken to limit the scope of the invention.

EXAMPLES

Example 1

Table 1 below indicates the mass ratio of raw material used in this example:

TABLE 1

| Example 1 |
| --- |
| 12% glucose |
| 88% glycerin |
| Brookfield viscosity at 25° C. |
| Max. 2,500 cps |

In a jacketed reactor, glycerin is added, and the temperature is raised up to 80° C. It is stirred for 40 minutes and soon after this it is slowly added to the glucose, since it has to be added very slowly to achieve good dispersion. It is mixed for 40 minutes until get homogeneous and with a Brookfield viscosity at 25° C. of 2,500 cps. After measuring the viscosity, the product has been found to have reached the parameters desired in the specification. It is important to leave it cool to fill the product, passing the same previously by a filter to remove impurities The obtained product was tested on hair, wherein the comparative results are illustrated in FIGS. 1 and 2, attached herewith.

FIG. 1 attached is a comparative graph of properties after applying and rinsing hair with the composition according to the invention and cyclopentasiloxane and dimethicone.

FIG. 2 attached is a comparative graph of properties after applying and rinsing dry hair with the composition according to the invention and cyclopentasiloxane and dimethicone.

To obtain the attached graphs, a panel was used where blind tests were performed by applying to each participant the product obtained as the example on half of the hair, wherein the other half had the silicone product applied.

It was asked for each volunteer to place a note for each attribute, for both (product according to the invention and silicone), ranging from 1 to 5, as explained below and whose results obtained are in the attached graphs:

note 1=Bad
note 2=Regular
note 3=Good
note 4=Very good
note 5=Excellent

This same methodology was employed in the other examples. In the case of example 4, the methodology was the same, except that the products were applied onto the skin.

Example 2

Table 2 below indicates the mass ratio of raw material used in this example:

TABLE 2

| Example 2 |
| --- |
| 9.3% glucose |
| 48% glycerin |
| 42.7% propylene glycol |
| Brookfield viscosity at 25° C. |
| Max. 400 cps |

In a jacketed reactor, glycerin is added, and the temperature is raised up to 90° C. Then, propylene glycol is added. It is stirred for 40 minutes and soon after this it is slowly added to the glucose, since it has to be added very slowly to achieve good dispersion. It is mixed for 40 minutes until get homogeneous and with a Brookfield viscosity at 25° C. of 400 cps. After measuring the viscosity, the product has been found to have reached the parameters desired in the specification. After this, the product can be filled, passing previously by a filter for removing the impurities.

Figure 3:
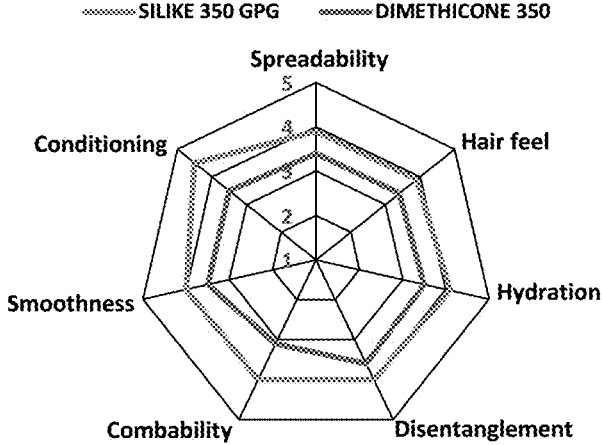
FIG. 3 represents a comparative graph of properties after applying and rinsing hair with the composition according to the invention and dimethicone 350.
Figure 4:
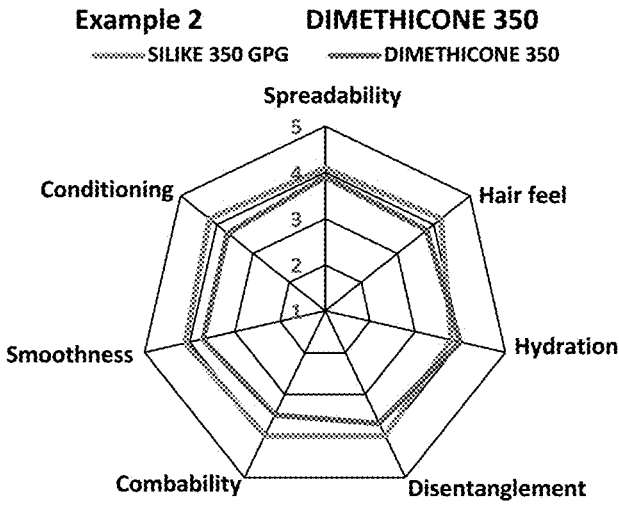
FIG. 4 is a comparative graph of properties after application and rinsing dry hair with the composition according to the invention and dimethicone 350.

The obtained product was tested on hair, wherein the comparative results are illustrated in FIGS. 3 and 4, attached herewith.

FIG. 3 is a comparative graph of properties after applying and rinsing hair with the composition according to the invention and dimethicone 350.

FIG. 4 is a comparative graph of properties after applying and rinsing dry hair with the composition according to the invention and dimethicone 350.

Example 3

Table 3 below indicates the mass ratio of raw material used in this example:

TABLE 3

| Example 3 |
| --- |
| 33.5% glucose |
| 66.5% propylene glycol |
| Brookfield viscosity at 25° C. |
| Max. 1,200 cps |

In a jacketed reactor, propylene glycol is added, and the temperature is raised up to 90° C. It is stirred for 50 minutes and soon after this it is slowly added to the glucose, since it has to be added very slowly to achieve good dispersion. It is mixed for 40 minutes until get homogeneous and with a Brookfield viscosity at 25° C. of 1,200 cps. After measuring the viscosity, the product has been found to have reached the parameters desired in the specification. After this, the product can be bottled, passing previously by a filter for removing the impurities.

Figure 5:
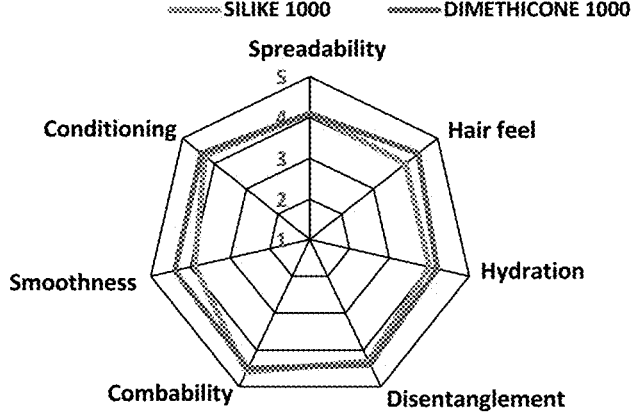
FIG. 5 is a comparative graph of properties after applying and rinsing hair with the composition according to the invention and dimethicone 1000.
Figure 6:
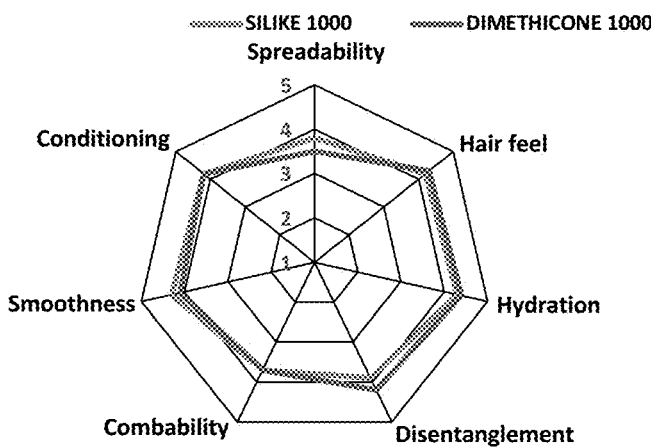
FIG. 6 is a comparative graph of properties after applying and rinsing dry hair with the composition according to the invention and dimethicone 1000.

The obtained product was tested on hair, wherein the comparative results are illustrated in FIGS. 5 and 6, attached herewith.

FIG. 5 is a comparative graph of properties after applying and rinsing hair with the composition according to the invention and dimethicone 1000.

FIG. 6 is a comparative graph of properties after applying and rinsing dry hair with the composition according to the invention and dimethicone 1000.

Example 4

Table 4 below indicates the mass ratio of raw material used in this example:

TABLE 4

| Example 4 |
| --- |
| 5% glucose |
| 40% glycerin |
| 55% propylene glycol |
| Brookfield viscosity at 25° C. |
| Max. 250 cps |

In a jacketed reactor, glycerin is added, and the temperature is raised up to 90° C. Then, propylene glycol is added. It is stirred for 40 minutes and soon after this it is slowly added to the glucose, since it has to be added very slowly to achieve good dispersion. It is mixed for 40 minutes until get homogeneous and with a Brookfield viscosity at 25° C. of 250 cps. After measuring the viscosity, the product has been found to have reached the parameters desired in the specification. After this, the product can be filled, passing previously by a filter for removing the impurities.

Figure 7:
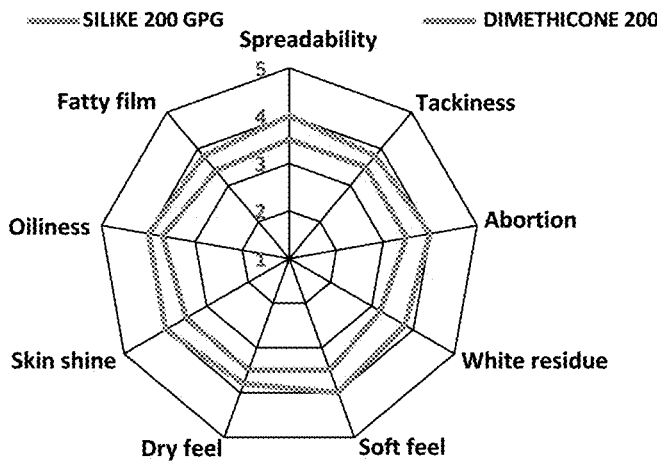
FIG. 7 shows the spreadability results of the product according to the invention relative to dimethicone 200.

The obtained product was tested on the skin, wherein the comparative results are illustrated in FIG. 7, attached herewith.

FIG. 7 is a comparative graph of spreadability of the composition according to the invention and dimethicone 200.

Example 5

Table 5 below indicates the mass ratio of raw material used in this example:

TABLE 5

| Example 5 |
| --- |
| 43.5% glucose |
| 56.5% propylene glycol |
| Brookfield viscosity at 25° C. |
| Max. 6,000 cps |

In a jacketed reactor, propylene glycol is added, and the temperature is raised up to 90° C. It is stirred for 40 minutes and soon after this it is slowly added to the glucose, since it has to be added very slowly to achieve good dispersion. It is mixed for 60 minutes until get homogeneous and with a Brookfield viscosity at 25° C. of 6,000 cps. After measuring the viscosity, the product has been found to have reached the parameters desired in the specification. Since this product is very viscous, it is necessary to bottle it with the same viscosity measurement temperature and always pass it through a filter to remove impurities.

Figure 8:
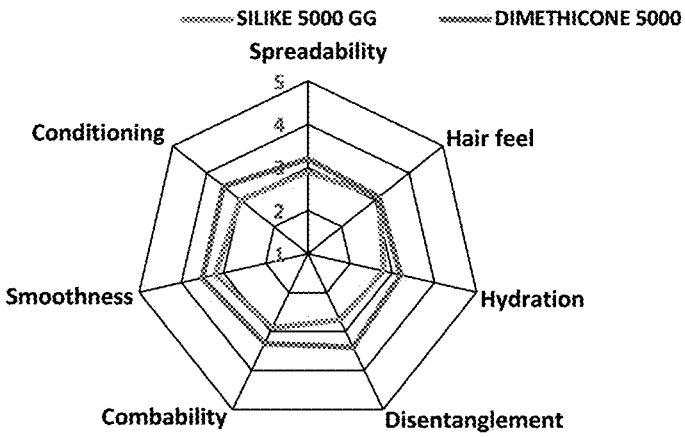
FIG. 8 is a comparative graph of properties after applying and rinsing hair with the composition according to the invention and dimethicone 5000.
Figure 9:
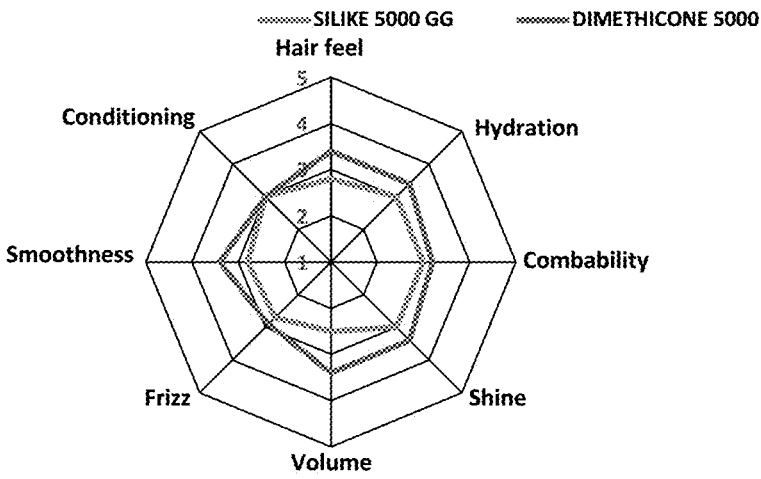
FIG. 9 is a comparative graph of properties after applying and rinsing dry hair with the composition according to the invention and dimethicone 5000.

The obtained product was tested on hair, wherein the comparative results are illustrated in FIGS. 8 and 9, attached herewith.

FIG. 8 is a comparative graph of properties after applying and rinsing hair with the composition according to the invention and dimethicone 5000.

FIG. 9 is a comparative graph of properties after applying and rinsing dry hair with the composition according to the invention and dimethicone 5000.

Example 6

Table 6 below indicates the mass ratio of raw material used in this example:

TABLE 6

| Example 6 |
| --- |
| 43% glucose |
| 57% propylene glycol |
| Brookfield viscosity at 25° C. |
| Max. 8,000 cps |

In a jacketed reactor, propylene glycol is added, and the temperature is raised up to 90° C. It is stirred for 40 minutes and soon after this it is slowly added to the glucose, since it has to be added very slowly to achieve good dispersion. It is mixed for 60 minutes until get homogeneous and with a Brookfield viscosity at 25° C. of 8,000 cps. Since this product is very viscous, it is necessary to bottle it with the same viscosity measurement temperature and always pass it through a filter to remove impurities.

Figure 10:
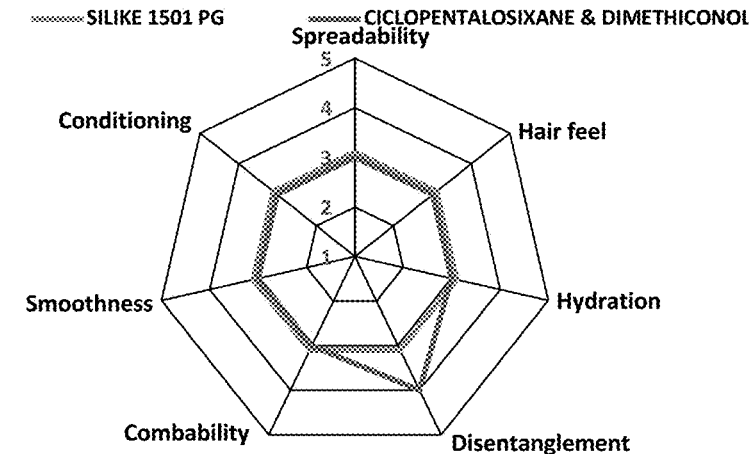
FIG. 10 is a comparative graph of properties after the applying and rinsing hair with the composition according to the invention and cyclopentasiloxane and dimethiconol.
Figure 11:
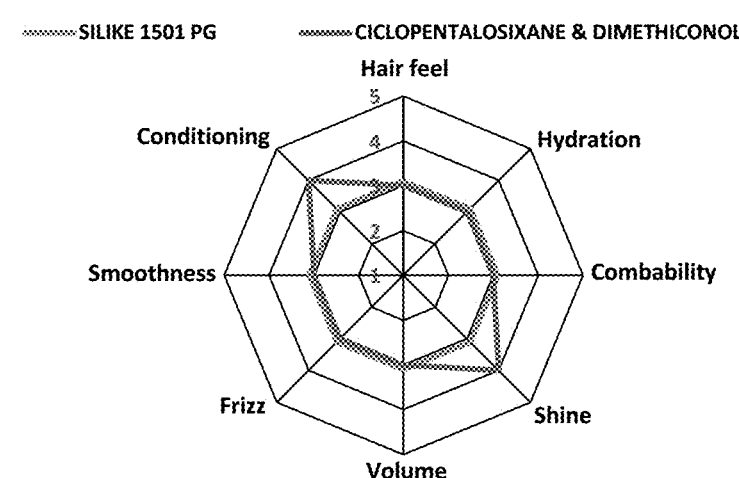
FIG. 11 is a comparative graph of properties after application and rinsing dry hair with the composition according to the invention and cyclopentasiloxane and dimethiconol.

The obtained product was tested on hair, wherein the comparative results are illustrated in FIGS. 10 and 11, attached herewith.

FIG. 10 attached herewith is a comparative graph of properties after applying and rinsing hair with the composition according to the invention and cyclopentasiloxane dimethiconol.

FIG. 11 attached herewith is a comparative graph of properties after applying and rinsing dry hair with the composition according to the invention and cyclopentasiloxane dimethiconol.

Example 7

Table 7 below indicates the mass ratio of raw material used in this example:

TABLE 7

| Example 7 |
| --- |
| 2% glucose |
| 30% of a 50% solution of cetrimonium chloride |
| 68% propylene glycol |

In a jacketed reactor, propylene glycol is added, and the temperature is raised up to 80° C. It is stirred for 40 minutes and soon after this it is slowly added to the glucose, since it has to be added very slowly to achieve good dispersion. It is mixed for 30 minutes, letting it get cold, until it gets homogeneous and with a Brookfield viscosity at 25° C. of 400 cps. After the addition of cetrimonium chloride, it is stirred for more 30 minutes. Soon after the product is ready to be filled, which is made by passing it through a filter to remove the impurities.

Figure 12:
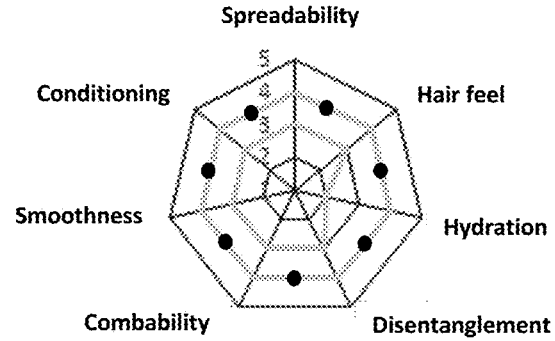
FIG. 12 is a comparative graph of properties after applying and rinsing hair with the composition according to the invention and cyclopentasilicone and dimethicone.
Figure 13:
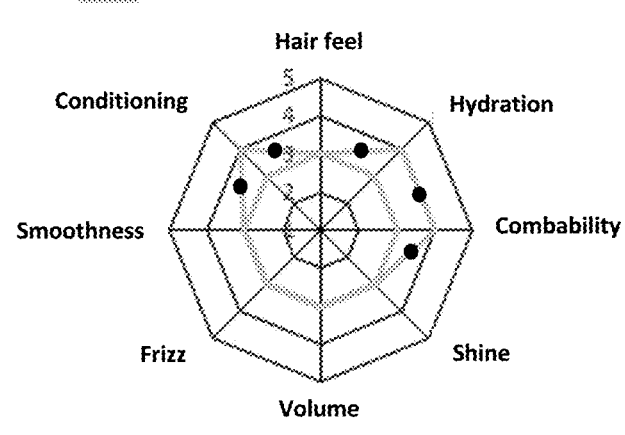
FIG. 13 is a comparative graph of properties after applying and rinsing dry hair with the composition according to the invention and cyclopentasilicone and dimethicone.

The obtained product was tested on hair, wherein the comparative results are illustrated in FIGS. 12 and 13, attached herewith.

FIG. 12 attached herewith is a comparative graph of properties after applying and rinsing hair with the composition according to the invention and amodimethicone and trideceth-12 and cetrimonium chloride.

FIG. 13 attached herewith is a comparative graph of properties after applying and rinsing dry hair with the composition according to the invention and amodimethicone and trideceth-12 and cetrimonium chloride.

Example 8

1. Introduction

Skin hydration is related to several mechanisms present in the epidermis and dermis and has an important influence on the physiology, mechanical properties of the skin and the homeostasis of healthy skin. Hydration depends on several factors such as, for example, the integrity of the stratum corneum of the epidermis and tight adhesion junctions between the keratinocytes to prevent water loss from the skin. Additionally, there are proteins and agents such as endogenous glycerol and hyaluronic acid present in the dermis and epidermis that contribute to skin hydration.

In this sense, the importance of water channels in the cell membrane that are called aquaporins and how they influence hydration was identified. 13 types of aquaporins have been identified in mammals. For human skin, the presence and importance of aquaporin 3 has been demonstrated by several studies. Aquaporin 3 is a water and glycerol channel present in keratinocytes of the epidermis. The lack of this channel when genetically manipulated in mice, led to reduced skin hydration and reduced skin elasticity. Additionally, it was observed that the expression of aquaporin 3 is affected by aging and continuous sun exposure that lead to reduced expression of this channel.

In patients with psoriasis lesions, a reduction in aquaporin 3 levels is observed.

Thus, the importance and relationship of aquaporin 3 with skin hydration is understood. Products can act on skin hydration through changes in aquaporin 3 expression, which reinforces the importance of researching this channel and its expression in human keratinocytes.

2. Objective

Evaluate the action of samples on aquaporin 3 levels using keratinocyte cell culture.

3. Relevance of the Study

The experimental conditions used are accepted and consistent with the methodologies currently applied in the international scientific community, as well as the use of cells under appropriate culture conditions.

4. Sample Description

Two samples were used:

| Sample name | Reference/ Batch | Internal Code In vitro nucleous | Manu- facture date | Storage conditions |
|---|---|---|---|---|
| DIMETHICONE 350 | NI | NV.73.02 | NI | Room Temperature |
| INVENTION 350 | NI | NV.74.02 | NI | Room Temperature |

*NI = not informed

Table 8 below indicates the mass ratio of the raw material used in this example to the sample of the composition used, hereinafter called INVENTION 350, which is the same as for example 2 and has the following composition:

TABLE 8

| Example 8 |
|---|
| 9.3% Glucose |
| 48% Glycerin |
| 42.7% Propylene |

5. Methodology

5.1 Cell Culture

In this study, human keratinocyte cells from the epidermis were used, maintained in culture with DMEM (Dulbecco's Modified Eagle's Medium) with the addition of supplements, in a stove at 37° C. and 5% $CO_2$ and manipulated inside the hood of laminar flow. In passage $O_3$ after thawing, the cells were distributed in 60 mm plates for the study.

5.2 Sample Preparation

Sample NV.73.02
  Sample preparation conditions in the starting solution: 10% of the sample in 90% of the culture medium;
  Additional procedures for solubilization: additional solubilization at 10% in culture medium for the final solution of the study;
  Aspect of the solubilized sample: fully solubilized.
  Expected sample concentrations (%): 0.1%
  Presence of additional solvent at the highest tested concentration of the sample: not applicable.
  pH measurement at the highest tested concentration of the sample: not determined.
Sample NV.74.02
  Sample preparation conditions in the starting solution: 10% of the sample in 90% of the culture medium;
  Additional procedures for solubilization: additional solubilization at 10% in culture medium for the final solution of the study;
  Aspect of the solubilized sample: fully solubilized.
  Expected sample concentrations (%): 0.1%
  Presence of additional solvent at the highest tested concentration of the sample: not applicable.
  pH measurement at the highest tested concentration of the sample: not determined.

5.3 Preparation of the Control Group

Control group: supplemented culture medium;

5.4 Evaluation of Hydration-Related Marker by Reverse Transcriptase Reaction Followed by Real-Time Polymerase Chain Reaction (RTq-PCR)

The solutions containing the control groups and samples were applied to the keratinocyte cell culture followed by an incubation in a stoven at 37° C. and 5% $CO_2$ for 24 hours. Afterwards, the extraction of messenger RNA with trizole was performed, evaluating its quantity and purity. From the messenger RNA, the reverse transcriptase reaction was performed to obtain the complementary strand of DNA. Then, analysis of aquaporin-3 was performed.

GAPDH was used as an endogenous control.

5.5 Analysis of Results

The results were evaluated using Microsoft Excel software.

For the analysis of the data obtained by RTq-PCR, the analysis from the 2^−ΔΔ Ct was used for graphic representation of the relative expression and statistical analysis from the ΔCt data. The control group was normalized to 1 and the other groups compared against it. Statistical analysis for comparison between groups was performed with T test and statistical significance level considered lower than 0.05.

6. Results

Figure 14:
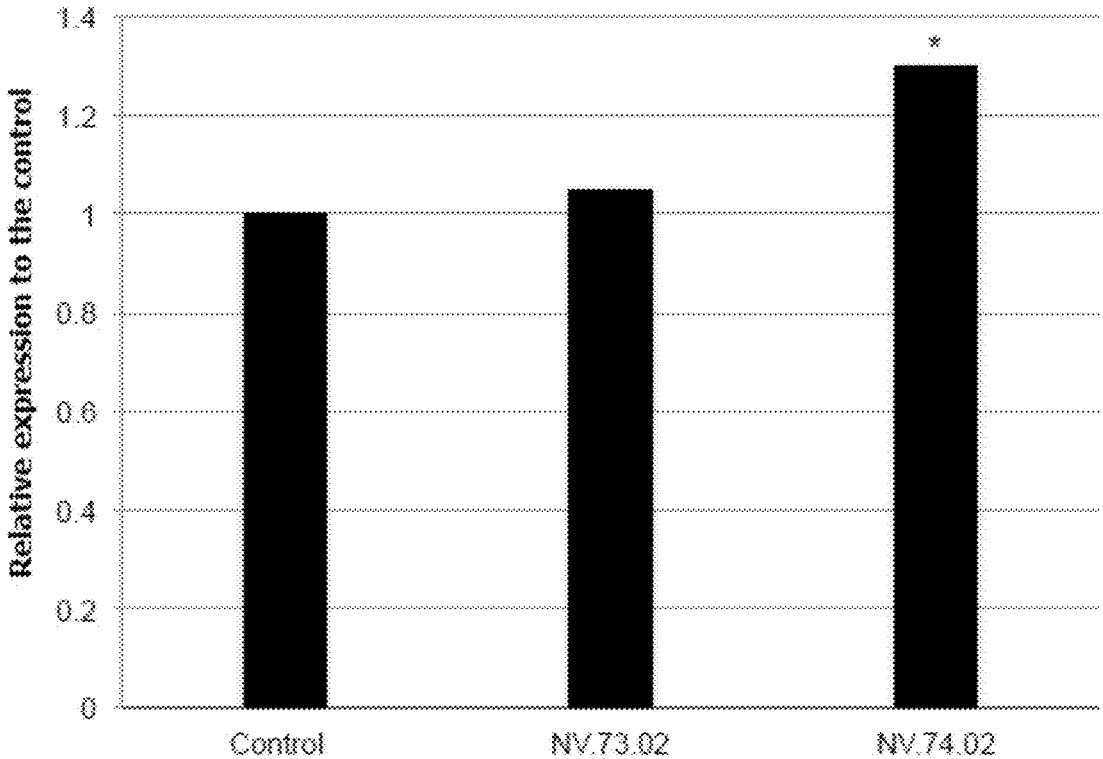
FIG. 14 demonstrates the hydration potential of the product according to the invention in comparison with dimethicone.

Using the RTq-PCR technique, the relative expression of aquaporin 3 was compared between the control groups, sample NV.73.02 and NV.74.02. FIG. 14, attached, demonstrates the relative expression presented after the analysis. The NV.73.02 group showed a 5% increase in aquaporin 3 expression when compared to the control group. The NV.74.02 group showed a 30% increase in aquaporin 3 expression when compared to the control group, and this difference was statistically significant (*p<0.05).

7. Conclusions

According to the results obtained, it is possible to state that:

Samples NV.73.02 and NV.74.02 increased the expression of aquaporin 3, which is related to increased hydration;

Comparing the samples evaluated, it was observed that the sample NV.74.02 showed a significant increase in the expression of aquaporin, this increase being greater when compared to the sample NV.73.02;

the attached FIG. 14 shows the hydration power of the products (NV.73.02 and NV.74.02) according to the present invention in comparison with dimethicone.

8. Opinion

In the study entitled "IN VITRO HYDRATION STUDY" referring to the DIMETHICONE 350 AND INVENCÃO 350 products, codes NV.73.02 and NV.74.02, it can be concluded that:

The products DIMETHICONE 350 AND INVENTION 350, codes NV.73.02 and NV.74.02, increase hydration by increasing aquaporin expression.

9. Notes

The results described herein are applicable only to the sample(s) tested, under the conditions and concentrations evaluated in this study.

The results presented are exclusively obtained from in vitro tests.

The invention claimed is:

1. A silicone substitute natural additive composition consisting of, in mass relative to the total mass of the composition:

(a) from 0.5% to 80% glucose;

(b) from 20% to 99.5% of a second component selected from the group consisting of propylene glycol, glycerin, and combinations thereof;

wherein the composition is a homogenous dispersion of (a) in (b), has a viscosity in a range of 250 cps to 8000 cps at 25° C., has properties similar to a silicone on dry hair or skin; and is free of silicones and water.

2. The silicone substitute natural additive composition according to claim 1, consisting of in mass relative to the total mass of the composition:

from 0.5% to 70% of glucose.

3. The silicone substitute natural additive composition according to claim 1, wherein the glucose is in the form of a dry glucose syrup.

4. The silicone substitute natural additive composition according to claim 1, consisting of in mass relative to the total mass of the composition:

12% wt/wt glucose; and

88% wt/wt propylene glycol and/or glycerin.

5. The silicone substitute natural additive composition according to claim 1, consisting of in mass relative to the total mass of the composition:

9.3% wt/wt glucose; and 90.7% wt/wt propylene glycol and/or glycerin.

6. The silicone substitute natural additive composition according to claim 1, consisting of in mass relative to the total mass of the composition:

33.5% wt/wt glucose; and 66.5% wt/wt propylene glycol and/or glycerin.

7. The silicone substitute natural additive composition according to claim 1, consisting of in mass relative to the total mass of the composition:

43% wt/wt glucose; and

57% wt/wt propylene glycol and/or glycerin.

8. The silicone substitute natural additive composition according to claim 1, consisting of in mass relative to the total mass of the composition:

5% wt/wt glucose; and

95% wt/wt propylene glycol and/or glycerin.

* * * * *